United States Patent
Takae et al.

(10) Patent No.: US 9,408,835 B2
(45) Date of Patent: Aug. 9, 2016

(54) PHARMACEUTICAL COMPOSITION FOR ORAL ADMINISTRATION

(71) Applicant: ASTELLAS PHARMA INC., Tokyo (JP)

(72) Inventors: Seiji Takae, Tokyo (JP); Hiroyuki Kojima, Tokyo (JP); Atsushi Sakurai, Tokyo (JP); Tetsuya Tamura, Tokyo (JP); Hiroaki Tasaki, Tokyo (JP); Atsushi Muro, Tokyo (JP)

(73) Assignee: ASTELLAS PHARMA INC., Tokyo (JP)

( * ) Notice: Subject to any disclaimer, the term of this patent is extended or adjusted under 35 U.S.C. 154(b) by 0 days.

(21) Appl. No.: 14/779,328

(22) PCT Filed: Mar. 28, 2014

(86) PCT No.: PCT/JP2014/059078
§ 371 (c)(1),
(2) Date: Sep. 22, 2015

(87) PCT Pub. No.: WO2014/157603
PCT Pub. Date: Oct. 2, 2014

(65) Prior Publication Data
US 2016/0045479 A1 Feb. 18, 2016

(30) Foreign Application Priority Data

Mar. 29, 2013 (JP) ................................. 2013-071361

(51) Int. Cl.
*A61K 31/437* (2006.01)
*A61K 9/20* (2006.01)
*A61K 9/28* (2006.01)

(52) U.S. Cl.
CPC ............. *A61K 31/437* (2013.01); *A61K 9/2054* (2013.01); *A61K 9/2095* (2013.01); *A61K 9/2806* (2013.01)

(58) Field of Classification Search
None
See application file for complete search history.

(56) References Cited

U.S. PATENT DOCUMENTS

| 8,163,767 B2 | 4/2012 | Inoue et al. |
| 8,779,140 B2 * | 7/2014 | Kikuchi .............. A61K 31/437 546/113 |
| 2005/0037067 A1 * | 2/2005 | Hovdal ................ A61K 9/2009 424/464 |
| 2013/0102628 A1 | 4/2013 | Kikuchi et al. |
| 2014/0171464 A1 | 6/2014 | Ishidoh et al. |

FOREIGN PATENT DOCUMENTS

| JP | 2004-131393 A | 4/2004 |
| WO | 2007-0077949 A1 | 7/2007 |
| WO | 2011-142478 A1 | 11/2011 |
| WO | 2012-002547 A1 | 1/2012 |

OTHER PUBLICATIONS

Japanese Patent Office; Office Action in Japanese Patent Appl. No. 2015-508747, dated Nov. 2, 2015; English translation of Notice of Reasons for Rejection.
International Search Report; PCT/JP2014/059078 dated Jun. 18, 2014.

* cited by examiner

*Primary Examiner* — Robert A Wax
*Assistant Examiner* — Quanglong Truong
(74) *Attorney, Agent, or Firm* — Kilpatrick Townsend & Stockton LLP

(57) ABSTRACT

A pharmaceutical composition containing, as the active ingredient, 4-{[(1R,2s,3S,5s,7s)-5-hydroxy-2-adamantyl]amino}-1H-pyrrolo[2,3-b]pyridine-5-carboxamide, of which the solubility in an acidic pH region is different from that in a neutral pH region, with rapid disintegration property and rapid drug dissolution property as well as the expectation of a good drug dosing compliance, is provided. The pharmaceutical composition for oral administration of the present invention contains 4-{[(1R,2s,3S,5s,7s)-5-hydroxy-2-adamantyl]amino}-1H-pyrrolo[2,3-b]pyridine-5-carboxamide or a pharmaceutically acceptable salt thereof, and a hydrophilic lubricant, and is useful as a pharmaceutical composition for oral administration with rapid disintegration property and rapid drug dissolution property as well as the expectation of a good drug dosing compliance.

10 Claims, No Drawings

PHARMACEUTICAL COMPOSITION FOR ORAL ADMINISTRATION

CROSS-REFERENCE TO RELATED APPLICATIONS

This application is a national phase application under 35 U.S.C. 371 claiming priority to PCT/JP2014/059078, filed Mar. 28, 2014, which application claims priority to JP 2013-071361, filed Mar. 29, 2013, the teachings of which are hereby incorporated by reference in their entireties for all purposes.

TECHNICAL FIELD

The present invention relates to a pharmaceutical composition for oral administration, comprising 4-{[(1R,2s,3S,5s,7s)-5-hydroxy-2-adamantyl]amino}-1H-pyrrolo[2,3-b]pyridine-5-carboxamide or a pharmaceutically acceptable salt thereof. Particularly, the present invention relates to a pharmaceutical composition for oral administration, comprising 4-{[(1R,2s,3S,5s,7s)-5-hydroxy-2-adamantyl]amino}-1H-pyrrolo[2,3-b]pyridine-5-carboxamide or a pharmaceutically acceptable salt thereof, and a hydrophilic lubricant, and having rapid disintegration property and rapid dissolution property.

BACKGROUND ART

It has been reported that 4-{[(1R,2s,3S,5s,7s)-5-hydroxy-2-adamantyl]amino}-1H-pyrrolo[2,3-b]pyridine-5-carboxamide (hereinafter sometimes referred to as compound A) has a superior Janus kinase 3 (hereinafter referred to as JAK3) inhibitory activity, and is useful as an active ingredient for an agent for treating and/or preventing diseases caused by undesirable cytokine signaling (for example, transplant rejection, autoimmune diseases, asthma, atopic dermatitis, Alzheimer's disease, atherosclerosis, rheumatism, and psoriasis) or diseases caused by abnormal cytokine signaling (for example, cancer and leukemia) (Patent literature 1).

Crystals in compound A or a pharmaceutically acceptable salt thereof with excellent stability in a solid state have been reported (Patent literature 2).

When compound A or a pharmaceutically acceptable salt thereof is provided as a medicament for treating or preventing diseases, its dose is appropriately determined depending on the individual case taking into consideration the route of administration, symptoms of the disease, age of the patient, race, sex, or the like. In the case of oral administration, the upsizing of its formulation is predicted in some daily doses of compound A or a pharmaceutically acceptable salt thereof (Patent literature 1).

On the other hand, for a compound to express its pharmacological effects, a pharmaceutical composition (formulation) is required to impart rapid disintegration property and rapid dissolution property to the formulation. Further, taking into consideration a drug dosing compliance in the future, the compactification (downsizing) of the formulation is desired.

A formulation containing canagliflozin as a specific drug at a high content and having a good drug dosing compliance is known (Patent literature 3). However, a pharmaceutical composition containing compound A or a pharmaceutically acceptable salt thereof at a high content is not disclosed.

Therefore, there is room for further study to provide a compact pharmaceutical composition for oral administration containing compound A or a pharmaceutically acceptable salt thereof and having rapid disintegration property and rapid dissolution property.

CITATION LIST

Patent Literature

[Patent literature 1] WO 2007/077949
[Patent literature 2] WO 2011/162300
[Patent literature 3] WO 2011/142478

SUMMARY OF INVENTION

Technical Problem

In order to provide a formulation containing compound A as an active ingredient, the present inventors selected the same pharmaceutical excipients as those used in a tablet in which rapid disintegration property had been confirmed in previous studies of formulations of a pharmaceutical composition containing compound A at a low content, and prepared tablets containing 150 mg as compound A (Comparative Example 1 described below). Since the obtained tablets contained a high content of compound A, the tablet size was large (tablet weight: 695.6 mg), and there was room for further improvement in terms of a drug dosing compliance. A disintegration test of the tablets was carried out using purified water, and a delay in disintegration time was observed in a tablet stored under open conditions. Next, the same pharmaceutical excipients as those used in Comparative Example 1 described below were used to prepare tablets of which the tablet size was compactified (Comparative Example 2 described below). A disintegration test of the obtained tablets was carried out using purified water, and a delay in disintegration time was observed in tablets. According to these results, the delay in disintegration time would cause a delay in the drug dissolution rate, and thus, there was a fear that it would lead to a decrease in bioavailability of compound A in the living body.

Compound A shows a large difference in solubility between an acidic pH range and a neutral pH range. More particularly, the solubility of compound A at an acidic pH range [in 1st fluid for dissolution test (JP1 (pH 1.2)) described in the Japanese Pharmacopoeia] was about 8,600 μg/mL, and the difference in the solubility at a neutral pH range [in 2nd fluid for dissolution test (JP2 (pH 6.8)) described in the Japanese Pharmacopoeia was about 8 μg/mL, and in pH 6.8 phosphate buffer described in the United States Pharmacopeia (USP) was about 11 μg/mL] was found to be about 1,000 times (about 12,500 μg/mL in water).

In the development of a compact pharmaceutical composition containing compound A or a pharmaceutically acceptable salt thereof and having rapid disintegration property and rapid dissolution property, the pH-dependent dissolution properties of compound A or a pharmaceutically acceptable salt thereof must be considered.

An object of the present invention is to provide a pharmaceutical composition for oral administration with rapid disintegration property and rapid dissolution property.

Another object of the present invention is to provide a pharmaceutical composition for oral administration in which a high content of compound A or a pharmaceutically acceptable salt thereof is contained, its dosage form is downsized, and a good drug dosing compliance can be expected.

Solution to Problem

The present inventors focused on the improvement of delay in disintegration time of a tablet, and conducted inventive studies to complete the present invention.

The present invention provides:

[1] a pharmaceutical composition for oral administration, comprising 4-{[(1R,2s,3S,5s,7s)-5-hydroxy-2-adamantyl]amino}-1H-pyrrolo[2,3-b]pyridine-5-carboxamide or a pharmaceutically acceptable salt thereof, and a hydrophilic lubricant;

[2] the pharmaceutical composition for oral administration of [1], wherein the hydrophilic lubricant is one, or two or more selected from the group consisting of sodium stearyl fumarate, polyethylene glycol, and sodium lauryl sulfate;

[3] the pharmaceutical composition for oral administration of [2], wherein the hydrophilic lubricant is sodium stearyl fumarate;

[4] the pharmaceutical composition for oral administration of any one of [1] to [3], further comprising a hydrophilic substance;

[5] the pharmaceutical composition for oral administration of [4], wherein the hydrophilic substance is one, or two or more selected from the group consisting of D-mannitol, erythritol, and xylitol;

[6] the pharmaceutical composition for oral administration of [5], wherein the hydrophilic substance is D-mannitol;

[7] the pharmaceutical composition for oral administration of any one of [1] to [6], wherein the content of the hydrophilic lubricant to the pharmaceutical composition for oral administration is about 0.1% by weight to 20% by weight;

[8] the pharmaceutical composition for oral administration of any one of [1] to [7], wherein the pharmaceutical composition for oral administration comprises a granulated product;

[9] the pharmaceutical composition for oral administration of [8], wherein the granulated product comprises a disintegrating agent;

[10] the pharmaceutical composition for oral administration of any one of [1] to [9], wherein its dosage form is tablets;

[11] the pharmaceutical composition for oral administration of any one of [1] to [10], wherein the disintegration time of the pharmaceutical composition for oral administration is within about 30 minutes in accordance with a disintegration test described in the Japanese Pharmacopoeia;

[12] the pharmaceutical composition for oral administration of any one of [1] to [11], wherein the disintegration time of the pharmaceutical composition for oral administration is within about 10 minutes in accordance with a disintegration test described in the Japanese Pharmacopoeia;

[13] the pharmaceutical composition for oral administration of any one of [1] to [12], wherein its dosage form is film-coated tablets; and

[14] a process of manufacturing a pharmaceutical composition for oral administration, comprising 4-{[(1R,2s,3S,5s,7s)-5-hydroxy-2-adamantyl]amino}-1H-pyrrolo[2,3-b]pyridine-5-carboxamide or a pharmaceutically acceptable salt thereof, and a hydrophilic lubricant.

Advantageous Effects of Invention

According to the present invention, a pharmaceutical composition for oral administration with rapid disintegration property and rapid dissolution property can be provided. Further, the present invention can provide a pharmaceutical composition for oral administration with a high content of compound A or a pharmaceutically acceptable salt thereof, a downsized dosage form, and the expectation of a good drug dosing compliance.

DESCRIPTION OF EMBODIMENTS

The term "rapid disintegration property" as used herein means that it disintegrates within 30 minutes in a disintegration test described in the Japanese Pharmacopoeia in an embodiment; that it disintegrates within 15 minutes in another embodiment; that it disintegrates within 10 minutes in still another embodiment; and that it disintegrates within 5 minutes in still yet another embodiment. In another embodiment, the term means that it disintegrates within 30 minutes in a dissolution test described in the Japanese Pharmacopoeia; that it disintegrates within 15 minutes in still another embodiment; and that it disintegrates within 10 minutes in still yet another embodiment.

More particularly, the disintegration test described in the Japanese Pharmacopoeia can be carried out, for example, as follows. Water is used as the test liquid. A basket-rack assembly equipped with glass tubes, in which a tablet is placed in each of the glass tubes, is attached to the central vertical shaft of an apparatus. This apparatus is placed in a beaker. The apparatus is adjusted so that the basket-rack assembly can be smoothly raised and lowered at a constant frequency rate between 29 and 32 cycles per minute through a distance between 53 mm and 57 mm. When the basket-rack assembly descends to the lowest point of the downward stroke, the distance between the wire mesh at the bottom of each tube and the bottom of the beaker is 25 mm. The volume of the test liquid in the beaker is such that when the basket-rack assembly descends to the lowest point of the downward stroke, the upper surface of the basket-rack assembly matches the surface of the test liquid. The temperature of the test liquid is maintained at 37° C.±2° C., and the time needed for disintegration of each tablet is measured. The time needed for disintegration of all the tablets is regarded as "disintegration time". The time needed for disintegration means the time needed to reach a state in which no residue of the sample is observed in the glass tube of the basket-rack assembly, or a state in which, if residue is observed, the residue is a soft mass not apparently having its original form, or fragments of insoluble coating or capsule shell.

More particularly, the dissolution test described in the Japanese Pharmacopoeia can be carried out in an embodiment as follows. A test liquid is equilibrated to 37° C.±0.5° C., and a tablet is placed in a vessel of an apparatus for a dissolution test. A paddle is rotated at a paddle speed of 50 rpm, and the time needed for disintegration of the tablet is measured. The time needed for disintegration means the time needed to reach a state in which no residue of the sample is observed in the vessel, or a state in which, if a residue is observed, the residue is a soft mass not apparently having its original form, or fragments of insoluble coating or capsule shell.

The term "rapid dissolution property" as used herein means, in an embodiment, that the dissolution rate of compound A is 85% or more after 30 minutes from the beginning of a dissolution test, method 2 (paddle method) described in the Japanese Pharmacopoeia, under the conditions using 900 mL of 0.1M HCl at a paddle speed of 50 rpm; and that the dissolution rate of compound A is 85% or more after 15 minutes from the beginning of the test in another embodiment. In still another embodiment, the term "rapid dissolution property" as used herein means, in an embodiment, that the dissolution rate of compound A is 10% or more after 30 minutes from the beginning of a dissolution test, method 2

(paddle method) described in the Japanese Pharmacopoeia, under the conditions using 900 mL of pH 6.8 phosphate buffer described in the United States Pharmacopeia (USP) at a paddle speed of 50 rpm; that the dissolution rate of compound A is 20% or more after 30 minutes from the beginning of the test in another embodiment; that the dissolution rate of compound A is 10% or more after 10 minutes from the beginning of the test in still another embodiment; that the dissolution rate of compound A is 20% or more after 10 minutes from the beginning of the test in still another embodiment; and that the dissolution rate of compound A is 30% or more after 10 minutes from the beginning of the test in still another embodiment. In connection with this, the pH 6.8 phosphate buffer shows a neutral pH range in which the solubility of compound A is extremely low.

The term "granulated product" as used herein means a product obtained by processing powder material consisting of a single or multi-component, using a binder or the like, into particles larger than the material. More particular, the term "granulated product" means a product obtained by processing at least compound A or a pharmaceutically acceptable salt thereof, as well as a hydrophilic substance if desired, using a binder, into particles larger than the material. The granulated product may further contain a disintegrating agent.

The particle size distribution of the granulated products may be represented by a particle size distribution measured by sieving out 1 to 10 g of the granulated products for 3 to 10 minutes, using a Ro-tap sieve shaker and standard sieves.

The average particle size of the granulated products may be represented by a diameter size of cumulative weight 50% (D50) calculated from a particle size distribution measured by sieving out 1 to 10 g of the granulated products for 3 to 10 minutes, using a Ro-tap sieve shaker and standard sieves.

Compound A as used herein is 4-{[(1R,2s,3S,5s,7s)-5-hydroxy-2-adamantyl]amino}-1H-pyrrolo[2,3-b]pyridine-5-carboxamide of the formula (I):

[Chem. 1]

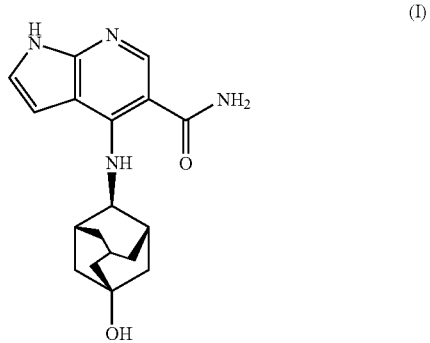

(I)

"Compound A hydrobromide" as used herein is a hydrobromide of 4-{[(1R,2s,3S,5s,7s)-5-hydroxy-2-adamantyl]amino}-1H-pyrrolo[2,3-b]pyridine-5-carboxamide. Compound A or compound A hydrobromide is readily available by the process described in patent literature 1 or 2, or in a similar manner thereto.

Compound A may form an addition salt with an acid. Such a salt is not limited, so long as it is a pharmaceutically acceptable salt. In an embodiment, examples thereof include acid addition salts with inorganic acids, such as hydrochloric acid, hydrobromic acid, sulfuric acid, nitric acid, and phosphoric acid, and acid addition salts with organic acids, such as succinic acid, fumaric acid, L-malic acid, L-tartaric acid, mesylic acid, and tosylic acid. The salt is a salt with hydrobromic acid in another embodiment, the salt is a salt with succinic acid in still another embodiment, and the salt is a salt with hydrochloric acid in still another embodiment.

Various hydrates or solvates, and crystal polymorphism of compound A or a pharmaceutically acceptable salt thereof may be used in the present invention. Compound A or a pharmaceutically acceptable salt thereof may be used as a single compound, or as a combination of two or more thereof.

Compound A or a pharmaceutically acceptable salt thereof has an inhibitory activity to JAK3, and is useful as an active ingredient for an agent for treating or preventing diseases caused by undesirable cytokine signaling (for example, transplant rejection, autoimmune diseases, asthma, atopic dermatitis, Alzheimer's disease, atherosclerosis, rheumatism, and psoriasis) or diseases caused by abnormal cytokine signaling (for example, cancer and leukemia).

The dose of compound A or a pharmaceutically acceptable salt thereof is appropriately determined depending on the individual case taking into consideration route of administration, symptoms of the disease, age of the patient, race, sex, or the like. In the case of oral administration, the appropriate daily dose of compound A or a pharmaceutically acceptable salt thereof is about 0.001 to about 100 mg/kg in an embodiment, about 0.1 to about 30 mg/kg in another embodiment, and about 0.1 to about 10 mg/kg in a still another embodiment, which is administered once or divided into two to four doses per day. The appropriate daily dose for intravenous administration is about 0.0001 to about 10 mg/kg, which is administered once or divided into several doses per day. The daily dose for a transmucosal drug is about 0.001 to about 100 mg/kg, which is administered once or divided into several doses per day.

The content of compound A or a pharmaceutically acceptable salt thereof per unit of the pharmaceutical composition of the present invention is about 10 mg to about 500 mg in an embodiment, and about 15 mg to about 200 mg in another embodiment. The content ratio of compound A or a pharmaceutically acceptable salt thereof per unit dosage form is, for example, about 5% by weight to about 80% by weight, about 5% by weight to about 70% by weight in an embodiment, about 20% by weight to about 50% by weight in another embodiment, about 20% by weight to about 80% by weight in still another embodiment, and about 30% by weight to about 60% by weight in still another embodiment.

The "hydrophilic lubricant" used in the present invention is not limited, so long as it can impart rapid disintegration property and rapid dissolution property to the pharmaceutical composition containing compound A or a pharmaceutically acceptable salt thereof. More particularly, for example, in an embodiment, it is a substance which can dissolve into 100 mL of water at an amount of 0.5 mg or more at 25° C.±5° C. In another embodiment, examples of the hydrophilic lubricant include sodium stearyl fumarate, polyethylene glycol (PEG: for example, product names PEG 4000, PEG 6000, and PEG 20000 (NOF Corporation)), sodium benzoate, sodium lauryl sulfate, and the like, and in still another embodiment, they include sodium stearyl fumarate, polyethylene glycol, and sodium lauryl sulfate. In still another embodiment, it is sodium stearyl fumarate.

The hydrophilic lubricant may be used as a single compound, or as a combination of two or more thereof.

The content of the hydrophilic lubricant is not limited, so long as it can impart rapid disintegration property and rapid dissolution property to the pharmaceutical composition containing compound A or a pharmaceutically acceptable salt thereof. More particularly, the content of the hydrophilic lubricant is, for example, about 0.1% by weight to about 20% by weight in the pharmaceutical composition in an embodiment, about 1% by weight to about 10% by weight in another embodiment, about 1% by weight to about 7% by weight in still another embodiment, about 1% by weight to about 5% by weight in still another embodiment, and about 2% by weight to about 5% by weight in still another embodiment.

As a state of the hydrophilic lubricant in the pharmaceutical composition, it is at a state where it is uniformly dispersed in the pharmaceutical composition in an embodiment, and at a state where it exists equally in the pharmaceutical composition in another embodiment. Since the hydrophilic lubricant is uniformly dispersed or exists equally in the pharmaceutical composition, a solution is easily permeated into the pharmaceutical composition, and rapid disintegration property and rapid dissolution property can be imparted to the pharmaceutical composition.

The pharmaceutical composition of the present invention may further contain a hydrophilic substance. The "hydrophilic substance" used in the present invention is not limited, so long as it is pharmaceutically acceptable, and can impart rapid disintegration property and rapid dissolution property to the pharmaceutical composition containing compound A or a pharmaceutically acceptable salt thereof. In an embodiment, examples of the hydrophilic substance include:

polymers having high water-solubility, such as polyethylene glycol (PEG; for example, product names PEG 4000, PEG 6000, and PEG 20000 (NOF Corporation)) and polyvinyl pyrrolidone (PVP; for example, product name PVP K30 (BASF)), sugar alcohols, such as D-mannitol, D-sorbitol, erythritol, xylitol, and the like, saccharides, such as saccharose, anhydrous maltose, D-fructose, dextran (for example, Dextran 40), glucose, and the like, surfactants, such as polyoxyethylene hydrogenated castor oil (HCO: for example, Cremophor RH40 (BASF), HCO-40, and HCO-60 (Nikko Chemicals Co., Ltd.)), polyoxyethylene polyoxypropylene glycol (for example, Pluronic F68 (ADEKA Corporation) and the like), polyoxyethylene sorbitan higher fatty acid esters (Tween (registered trademark): for example, Tween 80 (Kanto Chemical Co., Inc.)), and the like, salts, such as sodium chloride, magnesium chloride, and the like, organic acids, such as citric acid, tartaric acid, and the like, amino acids, such as glycine, β-alanine, lysine hydrochloride, and the like, and aminosaccharides, such as meglumine and the like. In another embodiment, examples of the hydrophilic substance include D-mannitol, erythritol, and xylitol, and in still another embodiment, examples of the hydrophilic substance include D-mannitol.

The hydrophilic substance may be used as a single compound, or as a combination of two or more thereof.

The content of the hydrophilic substance is not limited, so long as it can impart rapid disintegration property and rapid dissolution property to the pharmaceutical composition containing compound A or a pharmaceutically acceptable salt thereof. More particularly, the content of the hydrophilic substance is, for example, about 0.1% by weight to about 99% by weight in the pharmaceutical composition in an embodiment, about 10% by weight to about 70% by weight in another embodiment, and about 30% by weight to about 50% by weight in still another embodiment.

The pharmaceutical composition of the present invention may be an embodiment consisting of granulated products, and another embodiment in which one or more pharmaceutical excipients are added to granulated products.

Further, the pharmaceutical composition of the present invention may be a still another embodiment in which granulated products are compression-molded to prepare tablets, and a still another embodiment in which one or more pharmaceutical excipients are added to granulated products, and the resulting mixture is compression-molded to prepare tablets.

The granulated product means a product obtained by granulating at least compound A or a pharmaceutically acceptable salt thereof, as well as a hydrophilic substance if desired, using a binder. The granulated product may further contain a disintegrating agent.

The particle size distribution of the granulated products is not limited, so long as it can impart rapid disintegration property and rapid dissolution property to the pharmaceutical composition containing compound A or a pharmaceutically acceptable salt thereof. More particularly, the content of granulated products having a particle size of 75 μm or less with respect to the granulated products is, for example, 30% by weight or less in an embodiment, and 20% by weight or less in another embodiment.

The average particle size (diameter size of cumulative weight 50% (D50)) of the granulated products is not limited, so long as it can impart rapid disintegration property and rapid dissolution property to the pharmaceutical composition containing compound A or a pharmaceutically acceptable salt thereof. More particularly, the average particle size is, for example, about 100 to 300 μm in an embodiment, about 150 to 300 μm in another embodiment, and about 200 to 300 μm in still another embodiment.

The "disintegrating agent" which is contained in the granulated products of the present invention is not limited, so long as it can impart rapid dissolution property to the pharmaceutical composition containing compound A or a pharmaceutically acceptable salt thereof. More particularly, examples of the disintegrating agent include low substituted hydroxypropylcellulose, microcrystalline cellulose, crospovidone, sodium starch glycolate, croscarmellose sodium, corn starch, potato starch, carmellose calcium, and carmellose sodium in an embodiment; low substituted hydroxypropylcellulose and microcrystalline cellulose in another embodiment; and low substituted hydroxypropylcellulose in still another embodiment.

The disintegrating agent may be used as a single compound, or as a combination of two or more thereof.

The content of the disintegrating agent contained in the granulated products is not limited, so long as it is pharmaceutically acceptable, and can impart rapid dissolution property to the pharmaceutical composition containing compound A or a pharmaceutically acceptable salt thereof. More particularly, the content of the disintegrating agent is, for example, about 1% by weight to about 50% by weight in the granulated product in an embodiment, about 5% by weight to about 30% by weight in another embodiment, and about 5% by weight to about 20% by weight in still another embodiment.

In the pharmaceutical composition of the present invention, further various pharmaceutical excipients may be used, if desired. Such pharmaceutical excipients are not limited, so long as they are pharmaceutically acceptable and pharmacologically acceptable. Examples of the pharmaceutical excipients include binders, disintegrating agents, acidulants, foaming agents, sweetening agents, flavors, coloring agents, buffers, antioxidants, surfactants, glidants, and the like. The disintegrating agent may be contained, together with the granulated product, in the pharmaceutical composition, so long as the desired effects of the present invention are achieved. The pharmaceutical excipients other than the disintegrating agents described below may be contained in the granulated product, or may be contained together with the granulated product, so long as the desired effects of the present invention are achieved.

Examples of the binders include gum arabic, hypromellose, hydroxypropyl cellulose, hydroxyethyl cellulose, and the like.

Examples of the disintegrating agents contained together with the granulated product include corn starch, potato starch, carmellose calcium, carmellose sodium, low substituted hydroxypropylcellulose, microcrystalline cellulose, crospovidone, sodium starch glycolate, croscarmellose sodium, and the like, and low substituted hydroxypropylcellulose in an embodiment. The content of the disintegrating agent contained together with the granulated products is, for example, about 1% by weight to 10% by weight in the pharmaceutical composition.

Examples of the acidulants include citric acid, tartaric acid, malic acid, and the like.

Examples of the foaming agents include sodium hydrogen carbonate and the like.

Examples of the sweetening agents include saccharin sodium, dipotassium glycyrrhizinate, aspartame, stevia, somatin, and the like.

Examples of the flavors include lemon, lemon lime, orange, menthol, and the like.

Examples of the coloring agents include yellow ferric oxide, red ferric oxide, black iron oxide, food yellow No. 4, food yellow No. 5, food red No. 3, food red No. 102, food blue No. 3, and the like.

Examples of the buffers include citric acid, succinic acid, fumaric acid, tartaric acid, ascorbic acid, and salts thereof; glutamic acid, glutamine, glycine, aspartic acid, alanine, arginine, and salts thereof; magnesium oxide, zinc oxide, magnesium hydroxide, phosphoric acid, boric acid, and salts thereof; and the like.

Examples of the antioxidants include ascorbic acid, dibutyl hydroxytoluene, propyl gallate, and the like.

Examples of the surfactants include polysorbate 80, sodium laurylsulfate, polyoxyethylene hydrogenated castor oil, and the like.

Examples of the glidants include light anhydrous silicic acid and the like.

These pharmaceutical excipients may be appropriately added as a single compound, or as a combination of two or more thereof. The contents of these pharmaceutical excipients are not limited, so long as the desired effects of the present invention are achieved.

The dosage form of the pharmaceutical composition of the present invention is, for example, tablets in an embodiment, uncoated tablets or film-coated tablets in another embodiment, uncoated tablets in still another embodiment, and film-coated tablets in still another embodiment.

The weight of the pharmaceutical composition of the present invention is, for example, about 90 mg to about 690 mg in an embodiment, about 90 mg to about 600 mg in another embodiment, and about 90 mg to about 550 mg in still another embodiment.

Hereinafter a process of manufacturing the pharmaceutical composition of the present invention will be described, but the present invention is not limited thereto.

The pharmaceutical composition of the present invention can be produced in accordance with known methods per se, such as pulverization, mixing, granulation, forming (tabletting), film-coating, and the like.

Pulverization Step

The method of pulverization is not limited with respect to apparatus and procedures, so long as it is a conventional method in which pulverization can be pharmaceutically carried out. Examples of a pulverizer include a hammer mill, a ball mill, a jet mill, a pin mill, and the like. The conditions for pulverization may be appropriately selected and are not limited.

Mixing Step

The method of mixing is not limited with respect to apparatus and procedures, so long as it is a conventional method in which each component can be pharmaceutically and uniformly mixed. Examples of a mixer include a V type mixer, a ribbon type mixer, a container mixer, a high speed mixer, and the like. The conditions for mixing may be appropriately selected and are not limited.

Granulation Step

The method of granulation is not limited with respect to apparatus and procedures, so long as it is a conventional method in which granulation can be pharmaceutically carried out. Examples of a granulator include, for example, a fluidized bed granulator, a melting agitation granulator, a high-sheer mixing granulator, a pulverization granulator, an extrusion granulator, a tumbling fluidized bed granulator, a spray granulator, a dry granulator, and the like in an embodiment. Examples in another embodiment include a high-sheer mixing granulator. Examples of the method of granulation include a fluidized bed granulation method, a melting granulation method, a high-sheer mixing granulation method, a pulverization granulation method, an extrusion granulation method, a tumbling granulation method, a spray granulation method, a dry granulation method, and the like in an embodiment. Examples in another embodiment include a high-sheer mixing granulation method.

A binder liquid is prepared by dissolving or dispersing an appropriate binder in a solvent such as water, ethanol, methanol, or the like. These solvents may be used as an appropriate mixture.

The conditions for preparing a binder liquid may be appropriately selected and are not particularly limited.

The resulting granulated products may be dried. The method of drying is not limited, so long as it is a conventional method in which drying can be pharmaceutically carried out. Examples of the drying method include forced-air drying and drying under reduced pressure. The dried products may be sieved to remove large particles of a certain size or more from the products.

Forming Step

In the step of forming, granulated products, or a mixture of granulated products with various pharmaceutical excipients may be compression-molded using a rotary tabletting machine to prepare tablets.

The step of compression-molding is not limited with respect to apparatus and procedures, so long as it is a conventional method in which the pharmaceutical composition for oral administration of the present invention can be molded. Examples of the method include, for example, a direct tabletting method in which the drug is mixed with appropriate pharmaceutical excipients, and the mixture is compression-molded to obtain tablets, and a method in which granulated products are further mixed with a lubricant, and the mixture is compression-molded to obtain tablets.

Examples of the apparatus for tabletting include, for example, a rotary tabletting machine, a single punch tabletting machine, an oil press, and the like. The conditions for tabletting, such as tabletting pressure, are not limited, so long as it is tabletting pressure capable of molding tablets and avoiding damage to the tablets during the manufacturing process.

Film-Coating Step

After the tabletting, the surface of each tablet may be film-coated, if desired.

The method is not limited, so long as tablets can be pharmaceutically film-coated. Examples of the method include, for example, pan coating, dip coating, and the like.

Examples of film-coating bases include hypromellose, polyvinyl alcohol, polyvinyl alcohol copolymer, polyvinyl pyrrolidone, and the like.

Examples of plasticizers include, for example, polyethylene glycol, triethyl citrate, triacetin, and the like.

Examples of coloring agents include, for example, ferric oxide (red, yellow), black iron oxide, titanium oxide, and the like.

These film-coating bases, plasticizers, and coloring agents may be appropriately added as a single compound, or as a combination of two or more thereof, in appropriate amounts.

The film-coating rate is not limited, so long as a film is formed on the tablets.

After the film-coating, the coated products may be dried. The method of drying is not limited, so long as the products may be pharmaceutically dried. The conditions for drying are not limited, so long as they are appropriately determined taking into consideration, for example, the stability of tablets.

EXAMPLES

The present invention will now be further illustrated by, but is by no means limited to, the following Examples, Comparative Examples, and Test Examples. Compound A hydrobromide was prepared and used in accordance with the methods described in WO 2007/077949 and WO 2011/162300.

For the sake of convenience, concentration mol/L is represented as M. For example, 1M HCL means 1 mol/L HCl.

Example 1

According to the formulation table shown in Table 1, 4.006 kg of Compound A hydrobromide, 4.289 kg of D-mannitol (Pearlitol 50C (Roquette); the same compound was used unless otherwise specified.), 0.2889 kg of hydroxypropyl cellulose (HPC-L (Nippon Soda Co., Ltd.); the same compound was used unless otherwise specified.), 0.5264 kg of microcrystalline cellulose (CEOLUS PH101 (Asahi Kasei Chemicals Corporation); the same compound was used unless otherwise specified.), and 0.5264 kg of low-substituted hydroxypropyl cellulose (L-HPC LH21 (Shin-Etsu Chemical Co., Ltd.); the same compound was used unless otherwise specified.) were mixed using a high-share mixing granulator (PMA 65 High Shear Granulator (GEA); the same apparatus was used unless otherwise specified.). After mixing, the mixture was granulated adding an appropriate amount of water, and thereafter dried using a fluidized bed granulator (Niro Aeromatic Fluid bed dryer S-2 (Niro); the same apparatus was used unless otherwise specified.) to obtain a granulated product. Before and after drying, the granulated product was sieved using screen milling (Quadro mill 197S (Quadro Engineering)).

To 9.637 kg of the resulting granulated product, 0.5264 kg of low-substituted hydroxypropyl cellulose (L-HPC LH11 (Shin-Etsu Chemical Co., Ltd.)), 0.0514 kg of light anhydrous silicic acid (Aerosil 200 (Evonik); the same compound was used unless otherwise specified.), and 0.3146 kg of sodium stearyl fumarate (PRUV (JRS Pharma); the same compound was used unless otherwise specified.) were added, and mixed using a mixer (32 qt. V-shell blender (O'Hara technologies); the same apparatus was used unless otherwise specified.) to obtain a final blend (blend for tabletting).

The resulting blend for tabletting was compressed into tablets using a rotary tabletting machine (PICCOLA (RIVA); the same apparatus was used unless otherwise specified.) to obtain tablets (uncoated tablets) of the present invention.

The resulting uncoated tablets were film-coated using a film-coating machine (Labcoat-I (O'Hara technologies); the same apparatus was used unless otherwise specified.) to obtain tablets (film-coated tablets) of the present invention.

Example 2

According to the formulation table shown in Table 1, 4.006 kg of Compound A hydrobromide, 4.283 kg of D-mannitol, 0.288 kg of hydroxypropyl cellulose, 0.514 kg of microcrystalline cellulose, and 0.514 kg of low-substituted hydroxypropyl cellulose were mixed using a high-share mixing granulator. After mixing, the mixture was granulated adding an appropriate amount of water, and thereafter dried using a fluidized bed granulator to obtain a granulated product. Before and after drying, the granulated product was sieved using screen milling.

To 9.605 kg of the resulting granulated product, 0.514 kg of low-substituted hydroxypropyl cellulose (L-HPC LH11 (Shin-Etsu Chemical Co., Ltd.)), 0.0514 kg of light anhydrous silicic acid, and 0.514 kg of sodium stearyl fumarate were added, and mixed using a mixer to obtain a final blend (blend for tabletting).

The resulting blend for tabletting was compressed into tablets using a rotary tabletting machine to obtain tablets (uncoated tablets) of the present invention.

The resulting uncoated tablets were film-coated using a film-coating machine to obtain tablets (film-coated tablets) of the present invention.

Comparative Example 1

According to the formulation table shown in Table 1, tablets for comparison were obtained on a scale of 16,000 tablets in a similar way to the process of Example 1. Pharmatose 200M (DMV-Fonterra; the same compound was used unless otherwise specified.) was used as lactose, and magnesium stearate vegetable grade (Mallinckrodt; the same compound was used unless otherwise specified.) was used as magnesium stearate.

Comparative Example 2

According to the formulation table shown in Table 1, tablets for comparison were obtained on a scale of 25,800 tablets in a similar way to the process of Example 1.

Examples 3 to 5

According to the formulation table shown in Table 2, pharmaceutical excipients were added to the granulated product obtained in Example 1, and mixed using a polyethylene bag. The resulting blend for tabletting was compressed into tablets using an oil press to obtain tablets (uncoated tablets) of the present invention.

Kolliphor SLS Fine (BASF) was used as sodium laurylsulfate, and Polyglykol 8000 (Clariant) was used as polyethylene glycol.

Example 6

According to the formulation table shown in Table 2, Compound A hydrobromide, erythritol (Erythritol 100M, B Food Science Co., Ltd.)), hydroxypropyl cellulose, microcrystalline cellulose, and low-substituted hydroxypropyl cellulose were mixed using a pestle and a mortar. The mixture was granulated adding purified water. The resulting granulated product was dried and sieved, and low-substituted hydroxypropyl cellulose, light anhydrous silicic acid, and sodium stearyl fumarate were added and mixed. The resulting blend was compressed into tablets using an oil press to obtain tablets (uncoated tablets) of the present invention.

Example 7

According to the formulation table shown in Table 2, tablets (uncoated tablets) of the present invention were obtained in a similar way to the process of Example 6. Xylitol (KANTO CHEMICAL CO., INC.) was used.

Example 8

According to the formulation table shown in Table 3, tablets (uncoated tablets) of the present invention were obtained in a similar way to the process of Example 6.

TABLE 1

|  | Ex. 1 | Ex. 2 | Comp. Ex. 1 | Comp. Ex. 2 |
|---|---|---|---|---|
| Compound A hydrobromide | 187.2 | 187.2 | 187.2 | 187.2 |
| Lactose | — | — | 292.1 | 115.2 |
| D-Mannitol | 200.4 | 200.1 | — | — |
| Hydroxypropyl cellulose | 13.5 | 13.5 | 20.3 | 16.2 |
| Microcrystalline cellulose (PH101) | 24.6 | 24.0 | 33.8 | 27.0 |
| Low-substituted hydroxy-propyl cellulose (LH21) | 24.6 | 24.0 | 67.5 | 27.0 |
| Subtotal (mg) | 450.3 | 448.8 | 600.9 | 372.6 |
| Microcrystalline cellulose (PH102) | — | — | 33.8 | 27.0 |
| Low-substituted hydroxy-propyl cellulose (LH11) | 24.6 | 24.0 | 33.8 | 135.0 |
| Light anhydrous silicic acid | 2.4 | 2.4 | — | — |
| Magnesium stearate | — | — | 6.8 | 5.4 |
| Sodium stearyl fumarate | 14.7 | 24.0 | — | — |
| Weight of uncoated tablet (mg) | 492.0 | 499.2 | 675.3 | 540.0 |
| Film-coating agent (Opadry 03F42210) | 15.0 | 15.0 | 20.3 | 16.2 |
| Weight of film-coated tablet (mg) | 507.0 | 514.2 | 695.6 | 556.2 |
| Punch shape (mm) | 14 × 7.4 | 14 × 7.4 | 16.7 × 8.8 | 15 × 7.9 |

TABLE 2

|  | Ex. 3 | Ex. 4 | Ex. 5 | Ex. 6 | Ex. 7 |
|---|---|---|---|---|---|
| Compound A hydrobromide | 187.2 | 187.2 | 187.2 | 187.2 | 187.2 |
| D-Mannitol | 200.4 | 200.4 | 200.4 | — | — |
| Erythritol | — | — | — | 200.4 | — |
| Xylitol | — | — | — | — | 200.4 |
| Hydroxypropyl cellulose | 13.5 | 13.5 | 13.5 | 13.5 | 13.5 |
| Microcrystalline cellulose (PH101) | 24.6 | 24.6 | 24.6 | 24.6 | 24.6 |
| Low-substituted hydroxy-propyl cellulose (LH21) | 24.6 | 24.6 | 24.6 | 24.6 | 24.6 |
| Subtotal (mg) | 450.3 | 450.3 | 450.3 | 450.3 | 450.3 |
| Low-substituted hydroxy-propyl cellulose (LH11) | 24.6 | 24.6 | 24.6 | 24.6 | 24.6 |
| Light anhydrous silicic acid | 2.4 | 2.4 | 2.4 | 2.4 | 2.4 |
| Sodium stearyl fumarate | 4.8 | — | — | 14.7 | 14.7 |
| Sodium laurylsulfate | — | 14.7 | — | — | — |
| Polyethylene glycol | — | — | 14.7 | — | — |
| Weight of uncoated tablet (mg) | 482.1 | 492.0 | 492.0 | 492.0 | 492.0 |
| Punch shape (mm) | 14 × 7.4 | 14 × 7.4 | 14 × 7.4 | 14 × 7.4 | 14 × 7.4 |

TABLE 3

|  | Ex. 8 |
|---|---|
| Compound A hydrobromide | 187.2 |
| D-Mannitol | 57.8 |
| Hydroxypropyl cellulose | 13.5 |
| Microcrystalline cellulose (PH101) | 24.6 |
| Low-substituted hydroxy-propyl cellulose (LH21) | 24.6 |
| Subtotal (mg) | 307.7 |
| Low-substituted hydroxy-propyl cellulose (LH11) | 24.6 |
| Croscarmellose sodium | — |
| Light anhydrous silicic acid | 2.4 |
| Sodium stearyl fumarate | 14.7 |
| Weight of uncoated tablet (mg) | 349.4 |
| Punch shape (nun) | 9 |

Test Example 1

A dissolution test of the tablets (film-coated tablets) obtained in Examples 1 and 2 was carried out in accordance with a dissolution test, method 2 (paddle method) described in the Japanese Pharmacopoeia under the following conditions. The results are shown in Table 4.
Paddle method, 50 rpm
Test liquid: 0.1M HCl (pH 1.2) 900 mL
Temperature of test liquid: 37±0.5° C.
Sampling time: 15 minutes and 30 minutes

TABLE 4

|  | Ex. 1 | Ex. 2 |
|---|---|---|
| After 15 min. (%) | 99 | 96 |
| After 30 min. (%) | 102 | 101 |

As a result, the tablets of Examples 1 and 2 showed rapid dissolution property, in which almost 100% as compound A was dissolved after 15 minutes from the beginning of the test. Further, each tablet disintegrated within 10 minutes in the dissolution test, and showed rapid disintegration property.

Test Example 2

Tablets (film-coated tablets) obtained in Examples 1 and 2 were separately packaged in PTP (Press Through Package;

container material: polyvinyl chloride, cover material: aluminum foil) packages, and stored for one month under open conditions at a temperature of 40° C. and a relative humidity of 75%. After storage, a dissolution test of the stored tablets was carried out in a similar way to the test method described in Test Example 1. The results are shown in Table 5.

TABLE 5

|  | Ex. 1 | Ex. 2 |
|---|---|---|
| After 15 min. (%) | 94 | 92 |
| After 30 min. (%) | 101 | 98 |

As a result, the tablets of Examples 1 and 2 showed rapid dissolution property, in which almost 100% as compound A was dissolved after 15 minutes from the beginning of the test. Further, each tablet disintegrated within 10 minutes in the dissolution test, and showed rapid disintegration property.

Test Example 3

The tablets (uncoated tablets and/or film-coated tablets) obtained in Examples 1 to 8 and Comparative Examples 1 and 2 were used to measure a disintegration time in accordance with the disintegration test described in the Japanese Pharmacopoeia. Purified water was used as a liquid for disintegration test. The results are shown in Tables 6 and 7.

TABLE 6

|  | Ex. 1 | Ex. 2 | Comp. Ex. 1 | Comp. Ex. 2 |
|---|---|---|---|---|
| Uncoated tablet (min) | 1.7 | 2.3 | 2.2 | >30 |
| Film-coated tablet (min) | 3.6 | 4.8 | 9.3 | >30 |

TABLE 7

|  | Ex. 3 | Ex. 4 | Ex. 5 | Ex. 6 | Ex. 7 | Ex. 8 |
|---|---|---|---|---|---|---|
| Uncoated tablet (min) | 1.5 | 1.5 | 9.8 | 2.2 | 12.9 | 4.0 |

All the tablets (uncoated tablets and film-coated tablets) obtained in Examples 1 to 8 showed rapid disintegration property, in which each disintegrated within 15 minutes. By contrast, the tablets of Comparative Example 2 showed a disintegration time of 30 minutes or more, and did not show rapid disintegration property.

Test Example 4

Tablets (film-coated tablets) obtained in Example 1 and Comparative Example 1 were separately packaged in PTP (Press Through Package; container material: polyvinyl chloride, cover material: aluminum foil) packages, and stored for one month under open conditions at a temperature of 40° C. and a relative humidity of 75%. After storage, the stored tablets were used to measure a disintegration time in accordance with the disintegration test described in the Japanese Pharmacopoeia. Purified water was used as a liquid for disintegration test. The results are shown in Table 8.

TABLE 8

|  | Ex. 1 | Comp. Ex. 1 |
|---|---|---|
| Disintegration time (min) | 2.6 | >30 |

The tablet of Example 1 also showed rapid disintegration after storage. By contrast, the tablet of Comparative Example 1 disintegrated within 10 minutes before storage, but showed a disintegration time of 30 minutes or more after storage and did not show rapid disintegration property.

Test Example 5

A dissolution test of the tablets obtained in Example 1 (film-coated tablets) and Example 8 (uncoated tablets) was carried out in accordance with a dissolution test, method 2 (paddle method) described in the Japanese Pharmacopoeia under the following conditions. The results are shown in Table 9.

Paddle method, 50 rpm
Test liquid: USP pH 6.8 phosphate buffer 900 mL
Temperature of test liquid: 37±0.5° C.
Sampling time: 5 minutes, 10 minutes, and 20 minutes, and 30 minutes

TABLE 9

|  | Ex. 1 | Ex. 8 |
|---|---|---|
| After 5 min. (%) | 35 | 25 |
| After 10 min. (%) | 40 | 35 |
| After 20 min. (%) | 40 | 36 |
| After 30 min. (%) | 37 | 35 |

All the tablets of Examples 1 and 8 showed rapid and high dissolution rates in excess of the solubility (about 11 μg/mL) of compound A in the USP pH 6.8 phosphate buffer. In another disintegration test in which the test liquid used in the disintegration test carried out in Test Example 3 was replaced with the USP pH 6.8 phosphate buffer, all the tablets showed rapid disintegration property, more particularly, the film-coated tablets of Example 1 showed 3.6 minutes, and the uncoated tablets of Example 8 showed 4.8 minutes. Therefore, it is considered that high bioavailability of compound A in the living body can be achieved by adding one or more disintegrating agents to granulated products.

Test Example 6

The particle size distribution and the average particle size of the granulated products obtained in Examples 1 and 2 were measured using Sonic Sifter (sample amount: 10 g, and vibration time: 5 minutes). The results are shown in Table 10. The percentages of granulated products which had passed through the sieve of 75 μm were 20% by weight or less.

TABLE 10

|  | Ex. 1 | Ex. 2 |
|---|---|---|
| Particles (%) retained on 850 μm | 10.7 | 7.4 |
| Particles (%) retained on 425 μm | 29.1 | 18.8 |
| Particles (%) retained on 250 μm | 18.2 | 19.9 |
| Particles (%) retained on 150 μm | 11.4 | 14.4 |
| Particles (%) retained on 106 μm | 6.2 | 14.2 |

TABLE 10-continued

|  | Ex. 1 | Ex. 2 |
|---|---|---|
| Particles (%) retained on 75 μm | 9.1 | 12.1 |
| Particles (%) passing 75 μm | 15.2 | 13.2 |
| D50 (μm) | 259.9 | 213.7 |

INDUSTRIAL APPLICABILITY

The present invention can provide a pharmaceutical composition for oral administration, as an active ingredient, containing compound A or a pharmaceutically acceptable salt thereof, which has a superior JAK3 inhibitory activity, with rapid disintegration property and rapid dissolution property as well as the expectation of a good drug dosing compliance.

The invention claimed is:

1. A tablet for oral administration, comprising 4-{[(1R,2s,3S,5s,7s)-5-hydroxy-2-adamantyl]amino}-1H-pyrrolo[2,3-b]pyridine-5-carboxamide or a pharmaceutically acceptable salt thereof, and a hydrophilic lubricant, wherein the hydrophilic lubricant is one, or two or more selected from the group consisting of sodium stearyl fumarate, polyethylene glycol, and sodium lauryl sulfate, wherein the content of 4-{[(1R,2s,3S,5s,7s)-5-hydroxy-2-adamantyl]amino}-1H-pyrrolo[2,3-b]pyridine-5-carboxamide or a pharmaceutically acceptable salt thereof to the tablet for oral administration is about 30% by weight to about 60% by weight, wherein the content of the hydrophilic lubricant to the tablet for oral administration is 1% by weight to 10% by weight, and a hydrophilic substance wherein the hydrophilic substance is a sugar alcohol.

2. The tablet for oral administration according to claim 1, wherein the hydrophilic lubricant is sodium stearyl fumarate.

3. The tablet for oral administration according to claim 1, wherein the hydrophilic substance is one, or two or more selected from the group consisting of D-mannitol, erythritol, and xylitol.

4. The tablet for oral administration according to claim 3, wherein the hydrophilic substance is D-mannitol.

5. The tablet for oral administration according to claim 1, wherein the tablet for oral administration comprises a granulated product.

6. The tablet for oral administration according to claim 5, wherein the granulated product comprises a disintegrating agent.

7. The tablet for oral administration according to claim 1, wherein the disintegration time of the tablet for oral administration is within about 30 minutes in accordance with a disintegration test described in the Japanese Pharmacopoeia.

8. The tablet for oral administration according to claim 1, wherein the disintegration time of the tablet for oral administration is within about 10 minutes in accordance with a disintegration test described in the Japanese Pharmacopoeia.

9. The tablet for oral administration according to claim 1, wherein its dosage form is film-coated tablets.

10. A process of manufacturing a tablet for oral administration, comprising 4-{[(1R,2s,3S,5s,7s)-5-hydroxy-2-adamantyl]amino}-1H-pyrrolo[2,3-b]pyridine-5-carboxamide or a pharmaceutically acceptable salt thereof, and a hydrophilic lubricant, wherein the hydrophilic lubricant is one, or two or more selected from the group consisting of sodium stearyl fumarate, polyethylene glycol, and sodium lauryl sulfate, wherein the content of 4-{[(1R,2s,3S,5s,7s)-5-hydroxy-2-adamantyl]amino}-1H-pyrrolo[2,3-b]pyridine-5-carboxamide or a pharmaceutically acceptable salt thereof to the tablet for oral administration is about 30% by weight to about 60% by weight, wherein the content of the hydrophilic lubricant to the tablet for oral administration is 1% by weight to 10% by weight, and a hydrophilic substance wherein the hydrophilic substance is a sugar alcohol.

* * * * *